(12) United States Patent
Murphy et al.

(10) Patent No.: US 12,343,551 B2
(45) Date of Patent: Jul. 1, 2025

(54) MINIMUM NEURONAL ACTIVATION THRESHOLD TRANSCRANIAL MAGNETIC STIMULATION AT PERSONALIZED RESONANT FREQUENCY

(71) Applicant: PeakLogic, Inc., San Diego, CA (US)

(72) Inventors: Kevin Timothy Murphy, San Diego, CA (US); Michael Sean Murphy, San Diego, CA (US)

(73) Assignee: PeakLogic, Inc., San Diego, CA (US)

( * ) Notice: Subject to any disclaimer, the term of this patent is extended or adjusted under 35 U.S.C. 154(b) by 194 days.

(21) Appl. No.: 17/892,832

(22) Filed: Aug. 22, 2022

(65) Prior Publication Data
US 2023/0050715 A1    Feb. 16, 2023

Related U.S. Application Data

(63) Continuation of application No. 16/481,424, filed as application No. PCT/US2018/026972 on Apr. 10, 2018, now Pat. No. 11,420,071.

(Continued)

(51) Int. Cl.
*A61N 2/00* (2006.01)
*A61B 5/00* (2006.01)
(Continued)

(52) U.S. Cl.
CPC .............. *A61N 2/006* (2013.01); *A61B 5/318* (2021.01); *A61B 5/369* (2021.01); *A61N 2/02* (2013.01);
(Continued)

(58) Field of Classification Search
CPC .......... A61N 2/006; A61N 2/02; A61N 2/008; A61B 5/318; A61B 5/369; A61B 5/165; A61B 5/4064; A61B 5/4836
(Continued)

(56) References Cited

U.S. PATENT DOCUMENTS 4,583,190 A    4/1986  Salb
6,067,467 A    5/2000  John
(Continued)

FOREIGN PATENT DOCUMENTS

AU    2003210835 A1    9/2003
CA       3012463 A1    8/2017
(Continued)

OTHER PUBLICATIONS

Notification of Transmittal of The International Search Report and The Written Opinion of The International Searching Authority, or The Declaration; International Search Report; and Written Opinion of The International Searching Authority for corresponding International Application No. PCT/US2018/026972, dated Aug. 24, 2018, 12 pages.

(Continued)

*Primary Examiner* — Sunita Reddy
(74) *Attorney, Agent, or Firm* — DITTHAVONG, STEINER & MLOTKOWSKI

(57) ABSTRACT

A transcranial magnetic stimulation (TMS) treatment system is provided. The system includes a sensor device that senses EEG signals from a subject through one or more leads and a server device configured to receive EEG data corresponding to the subject. The server includes an analysis module configured to process the EEG data and determine a personalized resonant brain frequency and a minimum neuronal activation threshold of the subject based at least in part on EEG data corresponding to one or more leads of the sensor device. The analysis module is also configured to determine a TMS treatment protocol where the treatment protocol includes at least a frequency based on the personalized resonant brain frequency and an amplitude based on the minimum neuronal activation threshold. The system also includes a treatment device configured to deliver a TMS (Continued)

treatment to the subject based on the TMS treatment protocol received from the server.

14 Claims, 8 Drawing Sheets

Related U.S. Application Data

(60) Provisional application No. 62/524,349, filed on Jun. 23, 2017, provisional application No. 62/508,971, filed on May 19, 2017, provisional application No. 62/484,296, filed on Apr. 11, 2017.

(51) Int. Cl.
| | |
|---|---|
| *A61B 5/16* | (2006.01) |
| *A61B 5/318* | (2021.01) |
| *A61B 5/369* | (2021.01) |
| *A61N 2/02* | (2006.01) |

(52) U.S. Cl.
CPC ............ *A61B 5/165* (2013.01); *A61B 5/4064* (2013.01); *A61B 5/4836* (2013.01); *A61N 2/008* (2013.01)

(58) Field of Classification Search
USPC ...................................................... 600/9–15
See application file for complete search history.

(56) References Cited

U.S. PATENT DOCUMENTS

| | | | |
|---|---|---|---|
| 6,132,361 | A | 10/2000 | Epstein et al. |
| 6,254,536 | B1 | 7/2001 | Devito |
| 6,385,486 | B1 | 5/2002 | John et al. |
| 6,459,936 | B2 | 10/2002 | Fischell et al. |
| 6,463,328 | B1 | 10/2002 | John |
| 6,983,184 | B2 | 1/2006 | Price |
| 7,013,177 | B1 | 3/2006 | Whitehurst et al. |
| 7,024,247 | B2 | 4/2006 | Gliner et al. |
| 7,187,790 | B2 | 3/2007 | Sabol et al. |
| 7,422,555 | B2 | 9/2008 | Zabara |
| 7,440,806 | B1 | 10/2008 | Whitehurst et al. |
| 7,894,905 | B2 | 2/2011 | Pless |
| 7,914,468 | B2 | 3/2011 | Shalon et al. |
| 8,465,408 | B2 | 6/2013 | Phillips et al. |
| 8,475,354 | B2 | 7/2013 | Phillips et al. |
| 8,480,554 | B2 | 11/2013 | Phillips et al. |
| 8,585,568 | B2 | 11/2013 | Phillips et al. |
| 8,613,695 | B2 | 12/2013 | Von Ohlsen et al. |
| 8,690,748 | B1 | 4/2014 | Fu |
| 8,744,563 | B2 | 6/2014 | Yoshida |
| 8,870,737 | B2 | 10/2014 | Phillips et al. |
| 8,888,672 | B2 | 11/2014 | Phillips et al. |
| 8,888,673 | B2 | 11/2014 | Phillips et al. |
| 8,926,490 | B2 | 1/2015 | Phillips et al. |
| 8,961,386 | B2 | 2/2015 | Phillips et al. |
| 9,015,057 | B2 | 4/2015 | Phillips et al. |
| 9,037,224 | B1 | 5/2015 | Fu |
| 9,095,266 | B1 | 8/2015 | Fu |
| 9,272,159 | B2 | 3/2016 | Phillips et al. |
| 9,308,387 | B2 | 4/2016 | Phillips et al. |
| 9,446,259 | B2 | 9/2016 | Phillips et al. |
| 9,532,748 | B2 | 1/2017 | Denison et al. |
| 9,649,502 | B2 | 5/2017 | Phillips et al. |
| 9,713,729 | B2 | 7/2017 | Phillips et al. |
| 9,983,670 | B2 | 5/2018 | Coleman et al. |
| 10,065,048 | B2 | 9/2018 | Phillips et al. |
| 10,071,245 | B1 | 9/2018 | Phillips et al. |
| 10,357,660 | B2 | 7/2019 | Phillips et al. |
| 10,420,482 | B2 | 9/2019 | Jin |
| 10,420,953 | B2 | 9/2019 | Jin |
| 10,548,501 | B2 | 2/2020 | Phillips et al. |
| 2002/0007128 | A1* | 1/2002 | Ives ..................... A61B 5/372 600/15 |
| 2003/0149678 | A1 | 8/2003 | Cook |
| 2005/0115561 | A1 | 6/2005 | Stahmann et al. |
| 2005/0182288 | A1 | 8/2005 | Zabara |
| 2006/0265022 | A1 | 11/2006 | John et al. |
| 2007/0083245 | A1 | 4/2007 | Lamensdorf et al. |
| 2007/0142874 | A1 | 6/2007 | John |
| 2007/0161919 | A1 | 7/2007 | DiLorenzo |
| 2009/0287108 | A1 | 11/2009 | Levy |
| 2010/0113959 | A1 | 5/2010 | Pascual-Leone et al. |
| 2010/0210894 | A1 | 8/2010 | Pascual-Leone et al. |
| 2012/0221075 | A1 | 8/2012 | Bentwich |
| 2013/0289433 | A1 | 10/2013 | Jin et al. |
| 2014/0223462 | A1 | 8/2014 | Aimone et al. |
| 2014/0316230 | A1 | 10/2014 | Denison et al. |
| 2015/0105837 | A1 | 4/2015 | Aguilar Domingo |
| 2015/0112409 | A1 | 4/2015 | Hagedorn et al. |
| 2015/0351655 | A1 | 12/2015 | Coleman |
| 2016/0000348 | A1 | 1/2016 | Kitajo et al. |
| 2017/0043398 | A1 | 2/2017 | Yang et al. |
| 2017/0105645 | A1* | 4/2017 | Moses .................... A61N 2/004 |
| 2017/0367607 | A1 | 12/2017 | Agawal et al. |
| 2018/0056083 | A1* | 3/2018 | Jin ....................... A61B 5/4836 |
| 2019/0059771 | A1 | 2/2019 | Fu |

FOREIGN PATENT DOCUMENTS

| | | |
|---|---|---|
| CN | 101690659 A | 4/2010 |
| CN | 202875325 U | 4/2013 |
| CN | 104519953 B | 1/2017 |
| JP | H10262943 A | 10/1998 |
| JP | 2004135829 A | 5/2004 |
| JP | 2006110234 A | 4/2006 |
| JP | 2008516696 A | 5/2008 |
| WO | 97039796 A1 | 10/1997 |
| WO | 2006044793 A2 | 4/2006 |
| WO | 2012176790 A1 | 12/2012 |
| WO | 2018191310 A1 | 10/2018 |

OTHER PUBLICATIONS

Klimesch et al., "Enhancing cognitive performance with repetitive transcranial magnetic stimulation at human individual alpha frequency", The European journal of Neuroscience, vol. 17, Mar. 17, 2003, doi: 10.1046/i.1460-9568.2003.02517.x. PMID: 12653991, pp. 1129-1133.

Jin et al., "Electroencephalographic photic driving in patients with schizophrenia and depression", Biological psychiatry, 41(4), Published Feb. 1, 1997, http://dx.doi.org/10.1016/s0006-3223(96)00473-8; Retrieved from https://escholarship.org/uc/item/74w3g0cc, pp. 496-499.

Geller et al., "Slow magnetic stimulation of prefrontal cortex in depression and schizophrenia", Prog. Neuro-Psychopharmacol. & Biol. Psychiatry.1997, vol. 21, doi: 10.1016/s0278-5846(96)00161-3, pp. 105-110.

Jin et al., "Therapeutic Effects of Individualized Alpha Frequency Transcranial Magnetic Stimulation (αTMS) on the Negative Symptoms of Schizophrenia", Published: Oct. 27, 2005, Schizophrenia Bulletin, vol. 32, Issue 3, Jul. 2006, https://doi.org/10.1093/schbul/sbj020, pp. 556-561.

ECG and EEG Applications-Quick Reference Guide, Texas Instruments, 2012 (Year: 2012).

George et al., "Transcranial magnetic stimulation: A review of its evolution and current applications", Arch Gen Psychiatry, vol. 56(4), Apr. 1999, 22 pages.

Okamura et al., "EEG Modification Induced by Repetitive Transcranial Magnetic Stimulation", Journal of Clinical Neurophysiology, 18(4), 2001, pp. 318-325.

Sauvage et al., "Design and Construction of a Portable Transcranial Magnetic Stimulation (TMS) Apparatus for Migraine Treatment", Journal of Medical Devices, Mar. 2010, vol. 4, 6 pages.

Glicksohn et al., "Time Production and EEG Alpha Revisited", Article, NeuroQuantology, Mar. 2009, vol. 7, Issue 1, p. 138-151.

Hanslmayr et al., "Increasing Individual Upper Alpha Power by Neurofeedback Improves Cognitive Performance in Human Subjects", Applied Psychophysiology and Biofeedback, vol. 30, No. 1, Mar. 2005, 10 pages.

(56) References Cited

OTHER PUBLICATIONS

Sauseng et al., "EEG Alpha Synchronization and Functional Coupling During Top-Down Processing in a Working Memory Task", Human Brain Mapping 26:148-155(2005), 8 pages.
Ilmoniemi et al., "TMS and electroencephalography: Methods and current advances", Chapter 37, Jan. 2008, pp. 594-608.
Jin et al., "EEG Resonant Responses in Schizophrenia: a Photic Driving Study with Improved Harmonic Resolution", Schizophrenia Research 44 (2000) 213-220.
Kanda et al., "The clinical use of quantitative EEG in cognitive disorders", Dementia & Neuropsychologia Sep. 2009;3(3):195-203.
Manjarrez-Montes-DE-Oca et al., "El β-hidroxi-β-metilbutirato (HMB) como suplemento nutricional (I): metabolismo y toxicidad", Nutr Hosp. 2015;31(2), pp. 590-596. (English abstract included).
Arns et al., "EEG Phenotypes Predict Treatment Outcome to Stimulants in Children With ADHD", Research Report, Journal of Integrative Neuroscience, vol. 7, No. 3 (2008) 421-438.
Babiloni et al., "Pre- and Poststimulus Alpha Rhythms Are Related to Conscious Visual Perception: A High-Resolution EEG Study", Cerebral Cortex Dec. 2006; 16:1690-1700.
Birca et al., "Interaction between the flash evoked SSVEPs and the spontaneous EEG activity in children and adults", Clinical Neurophysiology 117 (2006) 279-288.

\* cited by examiner

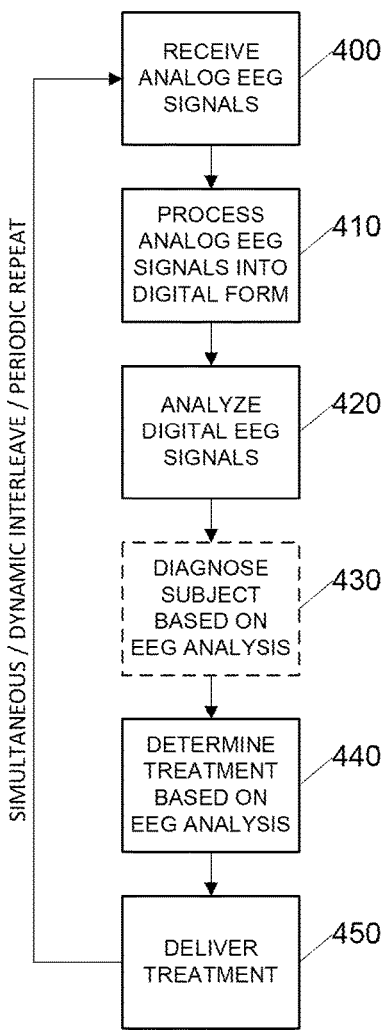
FIG. 4A
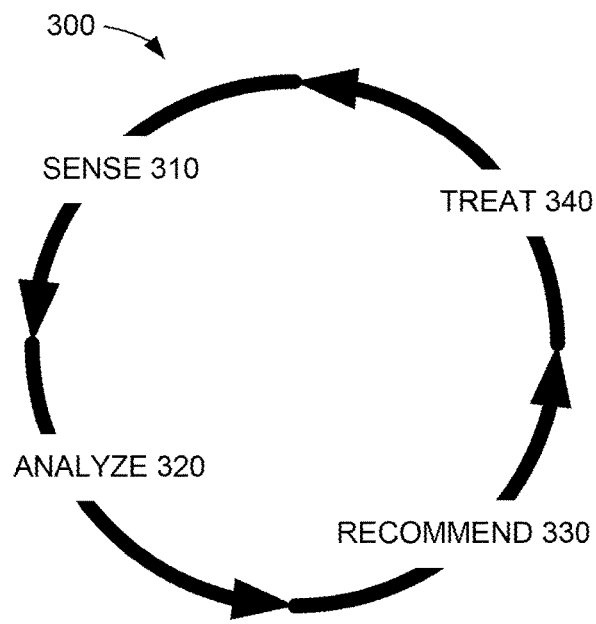
FIG. 3
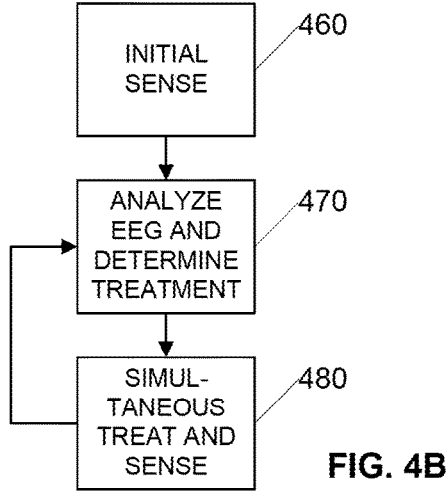
FIG. 4B
| 40 | Number of treatments |
| AB | Location(s) of treatments |
| 20% | Amplitude (percent of TMS coil power) |
| 10.5 | Frequency value for treatment (Hz) |
| 10s | Length of treatment |
| 30s | Length of rest interval between treatments |
FIG. 4C

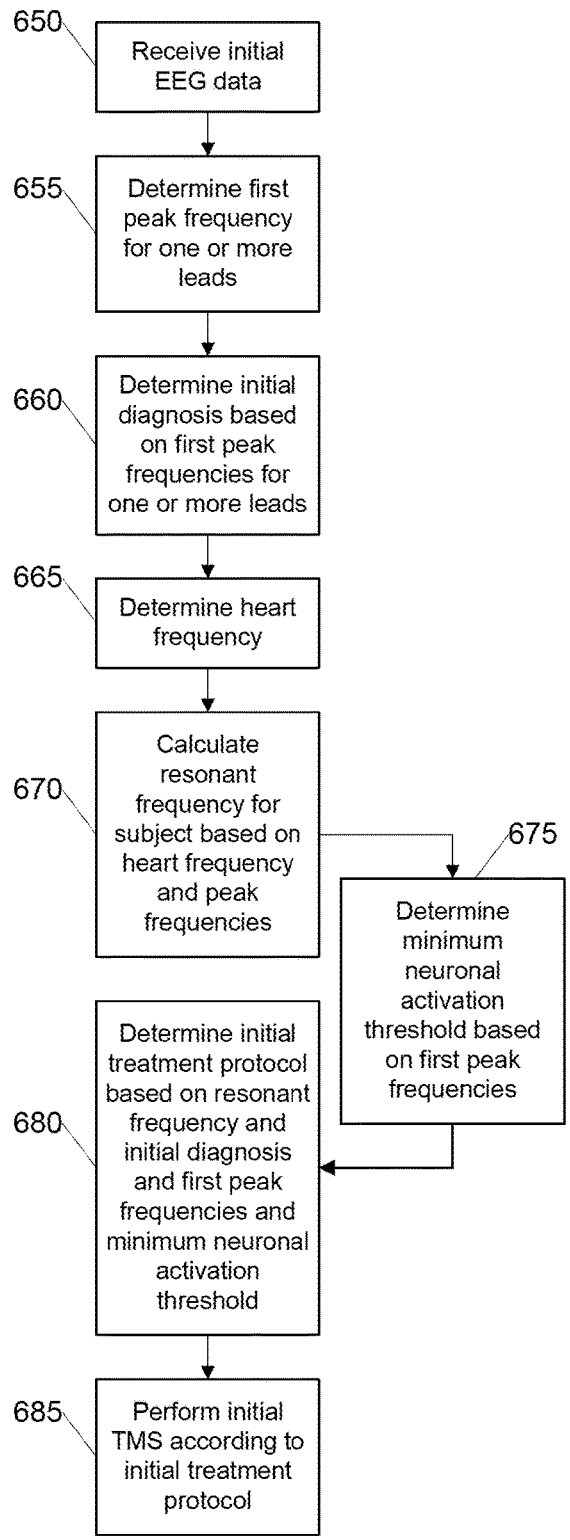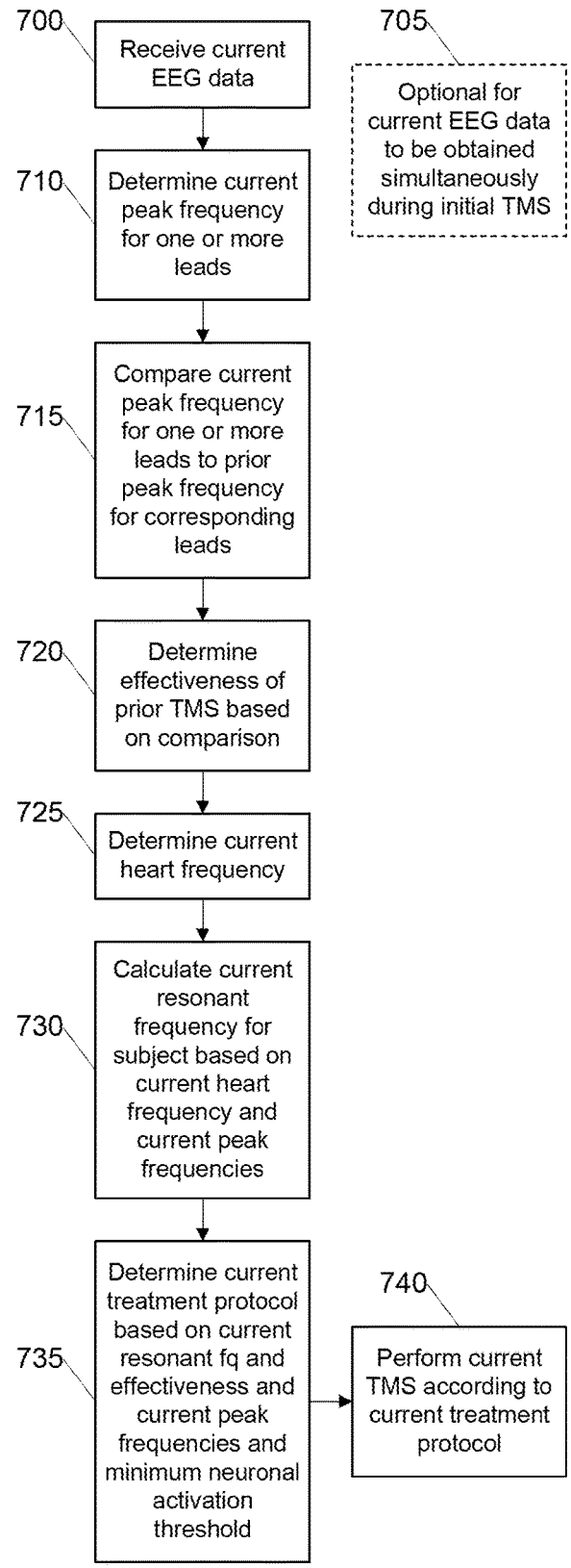
FIG. 4D
FIG. 4E

STARTING POINT – BASELINE EEG

ONE MONTH

TWO MONTHS
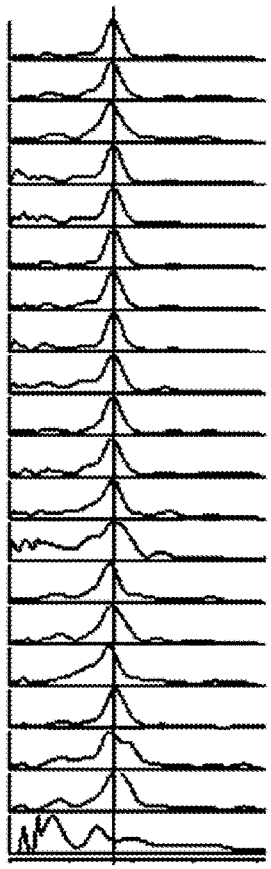
FIG. 5F
IDEAL ← coherence
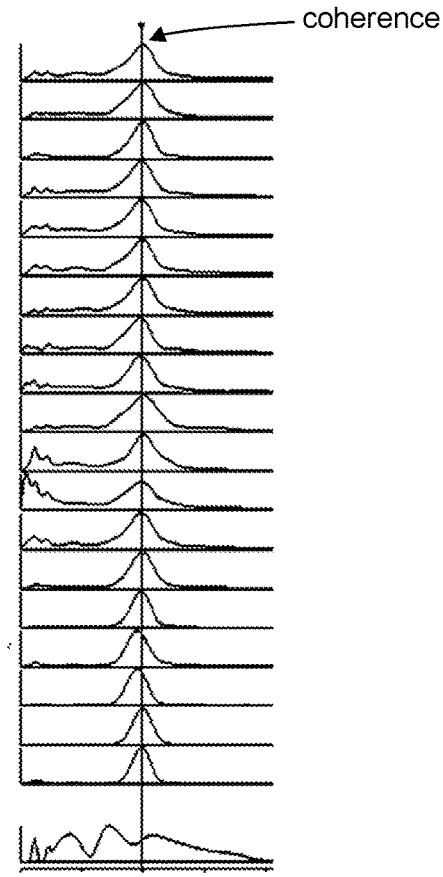
FIG. 5G
495 →
| TEST | WK 1 | WK 2 | WK 3 | WK 4 | WK 5 | WK 6 | WK 7 | WK 8 | WK 9 |
|---|---|---|---|---|---|---|---|---|---|
| PC | 52 | 29 | 20 | 19 | 16 | 6 | 4 | 2 | 1 |
| PCL-S | 59 | 45 | 43 | 32 | 25 | 16 | 9 | 2 | 2 |
| HAM-A | 32 | 24 | 20 | 15 | 9 | 7 | 5 | 1 | 1 |
| HAM-D | 35.5 | 23 | 21 | 20 | 14 | 8 | 4 | 1 | 1 |
| PSQI | 15 | 12 | 8 | 6 | 4 | 7 | 7 | 3 | 2 |
FIG. 5H

MINIMUM NEURONAL ACTIVATION THRESHOLD TRANSCRANIAL MAGNETIC STIMULATION AT PERSONALIZED RESONANT FREQUENCY

CROSS-REFERENCE TO RELATED APPLICATIONS

This application is a continuation of U.S. patent application Ser. No. 16/481,424, entitled "Minimum Neuronal Activation Threshold Transcranial Magnetic Stimulation at Personalized Resonant Frequency," filed on Jul. 26, 2019, which claims priority from PCT Application Serial No. PCT/US2018/026972, entitled "Minimum Neuronal Activation Threshold Transcranial Magnetic Stimulation at Personalized Resonant Frequency," filed on Apr. 10, 2018, which claims priority from U.S. Provisional Patent Application Ser. No. 62/484,296, filed on Apr. 11, 2017; U.S. Provisional Patent Application Ser. No. 62/508,971, filed on May 19, 2017; and U.S. Provisional Patent Application Ser. No. 62/524,349, filed on Jun. 23, 2017; the contents of which are hereby incorporated herein in their entirety by this reference.

BACKGROUND

Field of the Invention

The present invention generally relates to transcranial magnetic stimulation ("TMS") treatment and is more specifically directed toward treating a subject using TMS based on an analysis of the subject's electroencephalogram ("EEG") signals.

Related Art

TMS is a non-invasive procedure that is typically used for treating depression. During a TMS treatment session, an electromagnetic coil is positioned against a subject's scalp near the forehead and it generates a magnetic field that penetrates the cranium and stimulates nerve cells in the region of the subject's brain that is within the magnetic field. Although it is widely acknowledged in the medical community that the biology of how TMS works to treat depression is unknown, the Food and Drug Administration has nonetheless approved TMS for treatment of depression. However, because so little is understood about how TMS works, these treatments are often ineffective or even detrimental to a subject.

Additionally, the equipment needed to provide TMS treatment to a subject is typically located in hospitals or specialized medical facilities due to the size, weight and sensitive nature of the equipment. Accordingly, providing TMS treatment to subjects who are not in proximity of a treatment facility is not possible. Therefore, what is needed is a system and method that overcomes the significant challenges surrounding the use of TMS as described above.

SUMMARY

Described herein are systems and methods that solve the above described challenges surrounding the use of the TMS. In one embodiment, a static or mobile system for EEG based TMS treatment is provided. The system includes a server device that is configured to receive EEG data corresponding to a subject, where the EEG data comprises EEG signals received from a plurality of sensor leads of a sensor device. The server includes an analysis module configured to process the EEG data and determine a personalized resonant brain frequency of the subject (also referred to as a baseline brain frequency of the subject) based at least in part on EEG data corresponding to one or more leads of the sensor device. The analysis module is also configured to determine the TMS treatment protocol for the subject where the treatment protocol includes at least a frequency and an amplitude that is based on the personalized resonant brain frequency of the subject. The server also includes a treatment module configured to provide the TMS treatment protocol to a treatment device for delivery to the subject. The system may also include a power source that provides power to the server device, the sensor device and the treatment device. The power source may be an electricity grid, a battery, a power transmission infrastructure, or an engine of a mobile system for EEG based TMS treatment.

In an alternative embodiment, a system for EEG based TMS treatment is also provided. The system includes a server device that is configured to receive EEG data corresponding to a subject, where the EEG data comprises EEG signals for a plurality of sensor leads. The server includes an analysis module that is configured to analyze the EEG data and determine a peak brain frequency corresponding to at least two of the plurality of sensor leads. The server also includes a diagnosis module configured to analyze the peak brain frequency corresponding to the at least two of the plurality of sensor leads and determine a diagnosis for the subject. Advantageously, the diagnosis may include one of post traumatic stress disorder, autism, traumatic brain injury, irritable bowel syndrome, and heart arrhythmia.

In another alternative embodiment, a method for EEG based TMS treatment is provided. The method starts by positioning a static or mobile system for EEG based TMS treatment proximal to a subject and receiving EEG data corresponding to the subject, where the EEG data includes EEG signal information from each of a plurality of sensor leads. Next, the EEG data is analyzed to determine a personalized resonant brain frequency of the subject based at least in part on the EEG data corresponding to one or more leads of the sensor device. Next a TMS treatment protocol for the subject is determined based on at least the personalized resonant brain frequency of the subject, where the TMS treatment protocol includes at least a frequency and an amplitude. Finally, the TMS treatment protocol is delivered to the subject by a treatment device.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 3 is a flow diagram illustrating an example process for EEG based TMS treatment according to an embodiment of the invention;

FIG. 4A is a flow diagram illustrating an example process for EEG based TMS treatment according to an embodiment of the invention;

FIG. 4B is a flow diagram illustrating an example process for EEG based TMS treatment according to an embodiment of the invention;

FIG. 4C is a bock diagram illustrating an example TMS treatment protocol according to an embodiment of the invention;

FIG. 4D is a flow diagram illustrating an example process for an initial EEG based TMS treatment in a multi-treatment protocol according to an embodiment of the invention;

FIG. 4E is a flow diagram illustrating an example process for a current EEG based TMS treatment in a multi-treatment protocol according to an embodiment of the invention;

FIG. 5F is a graph diagram illustrating an example analog EEG data set from the subject of FIG. 5D converted into a digital EEG data set two months after the baseline EEG according to an embodiment of the invention;

FIG. 5G is a graph diagram illustrating an example ideal analog EEG data set converted into a digital EEG data set showing coherence according to an embodiment of the invention;

FIG. 5H is a block diagram illustrating an example set of neurobattery test scores for a subject during a 9 week treatment plan according to an embodiment of the invention;

DETAILED DESCRIPTION

Figure 1:
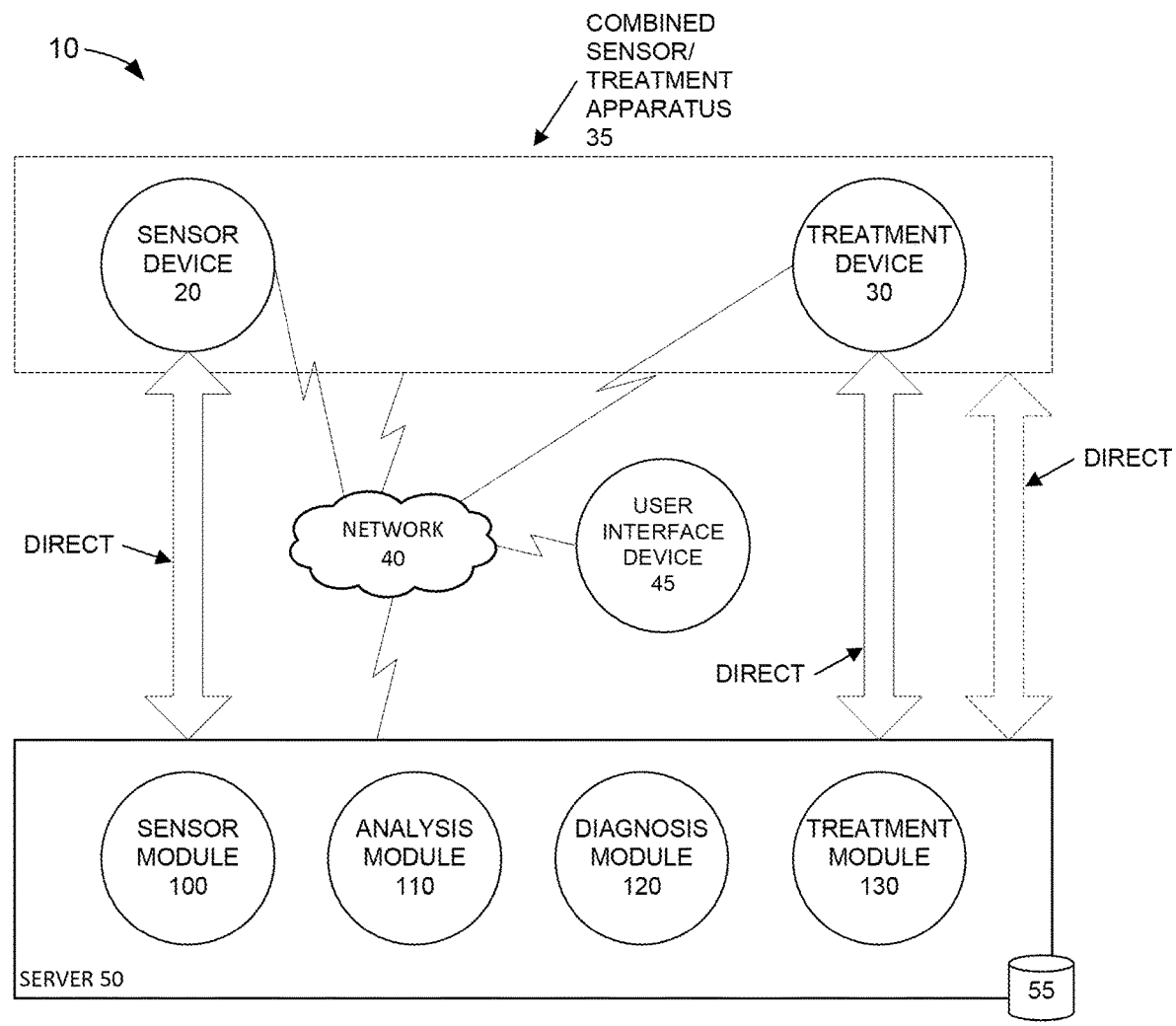
FIG. 1 is a network diagram illustrating an example system for EEG based TMS treatment according to an embodiment of the invention.

Certain embodiments disclosed herein provide for systems and methods for EEG based TMS treatment. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

INTRODUCTION

The inventors recognized certain problems with conventional TMS. A first problem is that the amplitude of the energy delivered to the human subject by TMS is exceedingly high. Conventional TMS relies upon overpowering the neurons with the exceedingly high treatment amplitude to force the neuron to activate at the desired frequency. The exceedingly high treatment amplitude causes overstimulation of the neurons. Overstimulation of the neurons in turn increases the refractory period for neurons, which is the time delay after which the neuron can activate again. Increasing the refractory period for neurons necessarily decreases the neuromodulatory effect, which is the ability for treatment to change the preferred activation frequency of the neuron.

Another problem with conventional TMS is that the exceedingly high treatment amplitude causes certain areas of the brain to be off limits to TMS treatment because conventional overstimulation may cause a seizure or other unintended consequences. For example, conventional TMS treatment of the motor strip is typically off limits.

The inventors recognized for the first time that TMS treatment at or slightly above the minimum neuronal activation threshold significantly improves the therapeutic response from the neurons of the subject because the neurons are not overstimulated and have a reduced refractory period and can be stimulated to activate many more times during treatment, which results in the neuron adapting to the preferred activation frequency of the neuron being delivered by the minimum neuronal activation threshold TMS. The use of minimum neuronal activation threshold TMS also allows treatment at locations that are off limits for conventional TMS.

Furthermore, the inventors recognized that processing and analyzing EEG data sensed simultaneously during TMS provides the ability to determine an individual subject's minimum neuronal activation threshold. The inventors also recognized that the optimum domain interval ("ODI") for a single lead in an EEG data set is an appropriate metric to determine or estimate the number of neurons activating (also referred to herein as "firing") at a particular frequency. The inventors also recognized that the composite domain interval ("CDI") across plural leads in an EEG data set determines the level of coherence in the brain of a subject. Coherence is when neurons from different regions of the brain are all activating at the same frequency. The inventors recognized that coherence across all regions of the brain is an ideal state for treatment of a wide assortment and variety of conditions. The inventors also recognized that neurobatteries are a tool that can be used to validate the success of TMS treatment.

The inventors also recognized that the correction rate of neurons is the rate at which the ODI of neurons from a particular region (e.g., sensed by a specific EEG lead) adopt and begin activating at the frequency of TMS treatment. The inventors recognized that higher correction rates correlate to the TMS treatment frequency being the same as the personalized resonant frequency of the subject. The inventors also recognized that the decay rate of neurons is the rate at which the ODI of neurons from a particular region (e.g., sensed by a specific EEG lead) return to a prior activation frequency after TMS treatment. The inventors recognized that slower correction rates correlate to the TMS treatment frequency being the same as the personalized resonant frequency of the subject.

Additional observations of the inventors include:

(1) the brain is evaluated and treated like any other organ system, which results in a large number of neurocognitive and neurodegenerative disorders being candidates for minimum neuronal activation threshold TMS.

(2) personalized resonance frequency of the brain can be further optimized in a wide range of the human population, which leads to performance enhancements and treatment of conditions such as autism and post-traumatic stress disorder.

(3) the brain prefers a harmonic state of synchronized waveforms. A balanced brain system with neurons across regions of the brain activating as the personalized resonance frequency results in a brain that is more energy efficient and more thermodynamically stable. Brain balance occurs side to side and back to front across all regions of the brain and a balanced brain system requires less cardiac output, less glucose metabolism, and is a preferred state at rest.

(4) EEG data provides a rapid and objective way to analyze a subject's brain's waveforms and determine the subject's brain's personalized resonance frequency.

(5) Hidden amongst a mixture of waveforms is a subject's brain's preferred, intrinsic, resonant frequency. EEG data can be processed to objectively calculate a subject's brain's personalized resonant frequency.

(6) During a time period, for example 24 hours, a subject's actual resonance frequency will fluctuate. Monitoring of a subject's actual resonance frequency allows notification of periods when the subject's actual resonance frequency is ideal and when it is not.

(7) The Occipital Cortex ("PPC") and visuo-spatial system is the predominant generator of brain rhythm and the brain state. PPC receives greater than 85% of all sensory information and pulses this magnetic signature to the anterior lobes (DLPFC).

(8) Trauma to the brain, either physical or emotional, impacts the brain's oscillatory mechanisms, creating disruptions in rhythm. Brain wave disruptions can be mild, temporary, and may normalize on their own, or can be more severe and, in accordance with the neuromodulatory effect, result in neurons that change their preferred activation frequency to a frequency other than the subject's personalized resonant frequency.

(9) In response to trauma, neurons typically slow their activation frequency as a form of self-preservation and tend to do so at different wavelengths. In some cases, neurons may increase their activation frequency, even in regions of the brain where other neurons are slowing activation frequency.

(10) The degree and severity of brain wave disruption corresponds to the severity of trauma, and also corresponds to a wide variety of phenotypes. Repetitive trauma to the brain is particularly deleterious to harmonic oscillations, creating "erroneous plasticity" where neurons, in accordance with the neuromodulatory effect, change their preferred activation frequency to a frequency other than the subject's personalized resonant frequency.

(11) objective analysis of EEG data closely correlates with commonly used psychometric neurobatteries, and are predictive of neurobehavior. Neurobatteries presently used for primary diagnosis are used to validate objective analysis of EEG data.

(12) Neuromodulation of the brain's waveforms is possible, and is most effective when TMS treatment is delivered at a subject's personalized resonant frequency. Disrupted brain waves become re-aligned to a stable and more balanced state over time with repetitive daily treatment at a subject's personalized resonant frequency.

Turning now to the drawings, FIG. 1 is a network diagram illustrating an example static or mobile system 10 for EEG based TMS treatment according to an embodiment of the invention. In the illustrated embodiment, the system 10 includes a sensor device 20 that is communicatively coupled with a server device 50. Communication between the sensor device 20 and the server device 50 may be direct (e.g., through a direct wired or wireless connection) or via a wired or wireless data communication network 40. The network 40 may be a private network or a public network or any combination of public and private networks including for example, the Internet. The sensor device 20 can be any type of device capable of sensing EEG information from a subject and providing the sensed EEG information (e.g., analog signals). In one embodiment, the sensor device 20 comprises one or more leads that each sense EEG information from a separate region of the brain of the subject.

The system 10 also includes a treatment device 30 that is communicatively coupled with the server device 50. Communication between the treatment device 30 and the server device 50 may be direct (e.g., through a direct wired or wireless connection) or via the previously described data communication network 40. The treatment device 30 can be any type of device capable of delivering transcranial magnetic stimulation to the brain cells and/or cerebral spinal fluid of a subject. In one embodiment, the treatment device 30 comprises a plurality of stimulators that each stimulate a separate region of the brain and/or cerebral spinal fluid of the subject.

In an alternative embodiment, the treatment device 30 comprises one or more visual cortex stimulators configured to stimulate the visual cortex or the retina and/or the optic nerve. In such a light based treatment device 30, the subject can be stimulated using an oscilloscope at the subject's personalized resonant frequency or by any other light wave stimulation device such as a tachistoscope. A visual stimulator may stimulate using visible light or light in the non-visible wavelengths. Another alternative for the treatment device 30 is a vibratory chamber, for example a water tank that vibrates a subject in the tank by vibrating the water in the tank. Advantageously, the treatment device 30 may comprise any sort of sensory stimulation device capable of delivering stimulation to the subject at the subject's personalized resonant frequency.

In one embodiment, the sensor device 20 and the treatment device 30 can be combined into a sensor/treatment apparatus 35 that is capable of both sensing EEG information from the brain of the subject and stimulating the brain of the subject. In one embodiment, the combined sensor/treatment apparatus 35 is a single integral unit and in an alternative embodiment the combined sensor/treatment apparatus 35 comprises a separate sensor device 20 and treatment device 30 that are worn simultaneously by the subject and operate simultaneously in connection with the server 50. The sensor device 20 can be moved around the calvarium.

In the illustrated embodiment, the server 50 comprises a sensor module 100, an analysis module 110, a diagnosis module 120 and a treatment module 130. The server 50 is also configured with a data storage area 55 that includes at least one non-transitory computer readable medium.

The sensor module 100 is configured to receive EEG data corresponding to a subject. The EEG data preferably comprises EEG information from one or more leads of a sensor device such as sensor device 20 or 35. The sensor module 100 is configured to store the EEG data in the data storage area 55. In one embodiment, the sensor module 100 is configured to receive analog EEG data (e.g., analog signals). In an alternative embodiment, the sensor module 100 is configured to receive digital EEG data (e.g., digital signals that were generated based on analog EEG signals). Additionally, the sensor module 100 is configured to instruct the sensor device 20 to begin sensing EEG data from the subject. This advantageously allows the server 50 to control the start time and duration that the sensor device 20 senses EEG data from the subject. In this fashion, the server 50 can cause the sensor device 20 to sense EEG data from the subject simultaneously or interleaved during treatment of the subject by the treatment device 30.

The analysis module 110 is configured to analyze the EEG data for a subject and generate a TMS treatment protocol for the subject based on the analysis of the subject's EEG data.

The diagnosis module 120 is configured to analyze the EEG data for a subject and generate a diagnosis of the subject based on the EEG data. In one embodiment, the diagnosis module is configured to identify a peak brain wave frequency for each of a plurality of leads in the EEG data. The diagnosis module is further configured to generate a diagnosis profile based on the peaks in the EEG data and compare the diagnosis profile to a normalized data set comprising classification profiles of previously established diagnoses based on the conventional standards of care to determine a diagnosis for the subject having a high confidence value based on similarities in the diagnosis profile to a classification profile for the determined diagnosis.

The treatment module 130 is configured to provide the TMS treatment protocol for delivery to the subject by a treatment device such as treatment device 30 or 35 generated by the analysis module 110. In one embodiment, the TMS module 130 may be configured to directly control the treatment device 30 for delivery of the TMS treatment protocol to the subject.

In one embodiment, the system 10 includes a user interface device 45. The user interface device 45 is configured to receive input from a subject. For example, in one embodiment the user interface device 45 is configured as a touch screen interface device that presents neuro-battery questions to a subject and receives responses from the subject. The neuro-battery responses are then provided to the server 50 via the network 40. The server 50, for example in the analysis module 110, analyzes the neuro-battery information for the subject along with other information related to the subject such as the EEG data to generate a TMS treatment protocol for the subject. In one embodiment, the user interface device 45 may be any type of device capable of downloading and installing an application (not shown) and the application is configured to present neuro-battery questions to a subject and receive responses from the subject and provide the responses to the neuro-battery questions to the server 50 via the network 40 or via a direct wired or wireless link.

Figure 2:
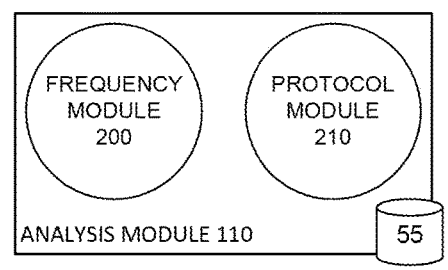
FIG. 2 is a block diagram illustrating an example analysis module according to an embodiment of the invention.

FIG. 2 is a block diagram illustrating an example analysis module 110 according to an embodiment of the invention. In the illustrated embodiment, the analysis module 110 comprises a frequency module 200 and a protocol module 210. The frequency module 200 is configured to analyze each lead in the EEG data and identify a peak frequency based on the EEG data for that lead. The frequency module 200 is also configured to analyze the peaks from the EEG data and determine a personalized resonant brain wave frequency for the subject.

Furthermore the frequency module 200 is configured to analyze EKG data (or other heart sensor data) to identify a heart frequency for the subject. Alternatively, the frequency module 200 may analyze EEG data for a particular lead (e.g., the A2 alpha wave lead) to estimate a heart frequency for the subject. In one embodiment, the frequency module 200 is configured to determine the personalized resonant brain wave frequency based on a combination of the EEG data and the heart frequency. For example, in one embodiment the most prominent alpha wave peak frequency in the EEG data may be divided by the heart frequency to determine the personalized resonant brain wave frequency.

The protocol module 210 is configured to determine a TMS treatment protocol for the subject. The objective of the TMS treatment protocol is to align the peaks identified in the EEG data at the same personalized resonant brain wave frequency. When the peaks from the one of more leads in the EEG data are aligned at the same personalized resonant brain wave frequency, this is referred to as coherence, as shown in FIG. 5G. Accordingly, the TMS treatment protocol may include, for example, a different amplitude for different stimulators on the treatment device. Additionally, the TMS treatment protocol may include variability amongst the individual treatment variables for the individual stimulators in the plurality of stimulators on the treatment device. Individual treatment variables that comprise a treatment protocol may include location, frequency, amplitude, magnetic field duration (e.g., stimulation ON), a no magnetic field duration (e.g., stimulation OFF) and a number of repeats. The treatment protocol will be discussed in more detail with respect to FIG. 4C.

FIG. 3 is a flow diagram illustrating an example process 300 for static or mobile EEG based TMS treatment according to an embodiment of the invention. In the illustrated embodiment, the treatment process begins with sensing EEG data from a subject in step 310. Next, the EEG data is received by the server and the EEG data is analyzed in step 320 to determine a TMS treatment protocol as previously described. Next, in step 330 the recommended treatment plan is provided to the physician who is responsible for treatment of the subject and is licensed to practice medicine where the subject is located. Upon receiving a confirmation of the treatment plan from the licensed physician who is thereby prescribing the TMS treatment to the patient, the TMS treatment protocol is provided for delivery to the subject by a TMS treatment device in step 340. Advantageously, these steps may be repeated week by week or day by day as shown in the illustrated embodiment.

FIG. 4A is a flow diagram illustrating an example process for static or mobile EEG based TMS treatment according to an embodiment of the invention. In one embodiment, the illustrated process may be implemented by a system such as previously described with respect to FIGS. 1-2. Initially in step 400, the system receives analog EEG signals and then processes those signals into digital form, for example using Discrete Fourier Transform or Fast Fourier Transform signal processing. Next, in step 420 the digital EEG signals are analyzed to identify a peak frequency for each lead included in the EEG signal data. Next, in optional step 430, a diagnosis for the subject based on a profile of the EEG lead peaks may be determined. The optional diagnosis step may also be performed at a later time. Next, in step 440, the system determines a TMS treatment protocol based on the EEG analysis. The TMS treatment protocol is designed to align the frequency peaks for each of the leads in the EEG signal data. Finally, in step 450 the TMS treatment protocol is provided for delivery to the subject by a TMS treatment device. Advantageously, in one embodiment the process may circle back to step 400 where analog EEG signals are received. In this iterative embodiment, a subject may be continuously evaluated and treated in real time by collecting EEG signals, analyzing the EEG signals, determining a TMS treatment protocol, delivering the TMS treatment protocol and repeating the same steps with little or no delay.

FIG. 4B is a flow diagram illustrating an example process for static or mobile EEG based TMS treatment according to an embodiment of the invention. In one embodiment, the illustrated process may be implemented by a system such as previously described with respect to FIGS. 1-2. Initially in step 460, the system performs an initial sensing of the subject, for example by instructing the sensor device to collect EEG signals through one or more of the various leads of the sensor device. Next, in step 470 the EEG data is analyzed to determine a TMS treatment protocol for the subject. Next, in step 480 the TMS treatment protocol is carried out to treat the subject and simultaneously additional sensing of the subject is carried out. The process then loops back and the additionally sensed EEG signals that are sensed while the subject is being simultaneously treated are analyzed and an adjusted TMS treatment protocol or the same TMS treatment protocol is determined in step 470. This analysis may advantageously take place during the current TMS treatment protocol. The process then continues again with step 480 and the adjusted TMS treatment protocol or the same TMS treatment protocol is carried out to treat the subject and simultaneously additional sensing of the subject is carried out. This process advantageously allows the mobile system to sense the subject and treat the subject simultaneously and in real time make adjustments to the TMS treatment protocol to achieve the desired results.

FIG. 4C is a bock diagram illustrating an example TMS treatment protocol 490 according to an embodiment of the invention. In the illustrated embodiment, the TMS treatment protocol comprises a number of treatments, location(s), amplitude, frequency, length of stimulation, and length of rest interval. For example, the TMS treatment protocol 490 includes 40 treatments where each treatment is at locations A and B and the amplitude of the treatment is 20% of the power of the coil in the TMS treatment apparatus. Each of the 40 treatments are delivered at 10.5 Hz for 10 seconds followed by a 30 second rest. Accordingly, the total TMS treatment will include 400 seconds of actual stimulation at locations A and B.

FIG. 4D is a flow diagram illustrating an example process for an initial EEG based TMS treatment in a multi-treatment protocol according to an embodiment of the invention. The illustrated method may be carried out by systems described herein with respect to FIGS. 1, 2, and 6-10. Initially, in step 650, the system receives initial EEG data and then in step 655 analyzes the initial EEG data to determine a first peak frequency for one or more leads of a sensor device. The first peak frequency may also be referred to as the optimum domain interval for a particular lead of the sensor device. Next, in step 660, the system determines an initial diagnosis for the subject based on the first peak frequencies for one or more leads. Next, in step 665, the system determines a heart frequency for the subject and in step 670, the system calculates a personalized resonant frequency of the brain of the subject based at least on an analysis of the heart frequency and the peak frequencies for one or more leads of the sensor device. Next, in step 675, the system determines a minimum neuronal activation threshold based on the first peak frequencies. Advantageously, this may be accomplished by systematically lowering the amplitude of TMS treatment until the first peak frequencies reflect insufficient neuronal recruitment at the target frequency. The minimum neuronal activation threshold corresponds to when the TMS treatment amplitude is too low to activate a sufficiently high number of neurons. Next, in step 680, the system determines a TMS treatment protocol based on the personalized resonant frequency, the initial diagnosis and the minimum neuronal activation threshold. The system may also determine the TMS treatment protocol based in part on the composite domain interval of the first peak frequencies, for example to influence the location of treatment. Next, in step 685, the system performs the initial TMS according to the initial treatment protocol.

FIG. 4E is a flow diagram illustrating an example process for a current EEG based TMS treatment in a multi-treatment protocol according to an embodiment of the invention. The illustrated method may be carried out by systems described herein with respect to FIGS. 1, 2, and 6-10. Initially, in step 700, the system receives current EEG data. In one embodiment, the current EEG data may be collected during performance of initial TMS treatment or during performance of a prior TMS treatment as indicated in 705. Next, in step 710 the system analyzes the current EEG data to determine a current peak frequency for one or more leads of a sensor device. The current peak frequency may also be referred to as the optimum domain interval for a particular lead of the sensor device. Next, in step 715, the system compares the current peak frequencies (e.g., the current composite domain interval) to the prior peak frequencies for corresponding leads (e.g., the initial or prior composite domain interval). Next, in step 720, the system determines an effectiveness of the prior or initial TMS treatment based on the comparison in step 715. Next, in step 725, the system determines a heart frequency for the subject and in step 730, the system calculates a current personalized resonant frequency of the brain of the subject based at least on an analysis of the current heart frequency and the current peak frequencies for one or more leads of the sensor device. Next, in step 735, the system determines a TMS treatment protocol based on the current personalized resonant frequency and the effectiveness of the initial or prior TMS treatment and the minimum neuronal activation threshold. The system may also determine the TMS treatment protocol based in part on the composite domain interval of the first peak frequencies, for example to influence the location of treatment. Next, in step 740, the system performs the current TMS treatment according to the current treatment protocol.

Figure 5A:
FIG. 5A is a graph diagram illustrating an example pre-treatment analog EEG data set of a subject according to an embodiment of the invention.

FIG. 5A is a graph diagram illustrating an example pre-treatment analog EEG signal data set for a subject according to an embodiment of the invention. In the illustrated embodiment, the EEG signal data set includes EEG signals for a plurality of leads, namely (n) leads.

Figure 5B:
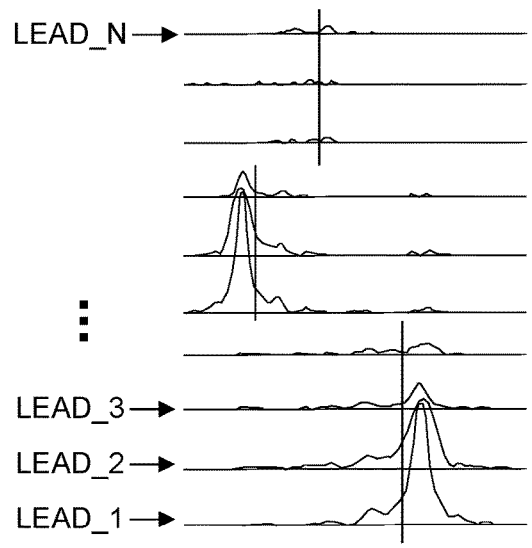
FIG. 5B is a graph diagram illustrating the example pre-treatment analog EEG data set of FIG. 5A converted into a digital EEG data set according to an embodiment of the invention.

FIG. 5B is a graph diagram illustrating the example pre-treatment analog EEG data set of FIG. 5A converted into a digital EEG data set according to an embodiment of the invention. As shown in the illustrated embodiment, the various leads each have a frequency peak with a different amplitude, where the amplitude of some peaks are higher than other peaks. Advantageously, the alpha wave peaks near the bottom are the strongest and have the highest amplitude. As additionally shown in the illustrated embodiment, the various leads also have their respective peaks at different frequencies, which results in the respective peaks not being in vertical alignment. Accordingly, an optimal TMS treatment protocol is designed to stimulate the various regions of the brain corresponding to the leads in the EEG data set in order to align the respective peaks and result in the various regions of the brain being at the same frequency.

Figure 5C:
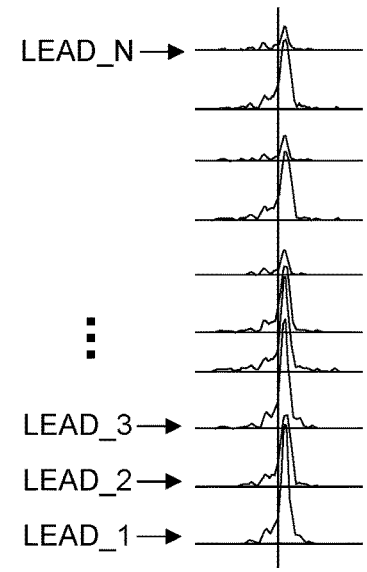
FIG. 5C is a graph diagram illustrating an example post-treatment analog EEG data set of the subject of FIG. 5A converted into a digital EEG data set according to an embodiment of the invention.

FIG. 5C is a graph diagram illustrating an example post-treatment analog EEG data set of the same subject converted into a digital EEG data set according to an embodiment of the invention. As can be seen in the illustrated embodiment, after delivery of the treatment protocol by a TMS treatment device, the respective peaks for the various leads in the EEG data are vertically aligned, demonstrating that the post treatment regions of the brain corresponding to the various leads are at substantially the same frequency.

Figure 5D:
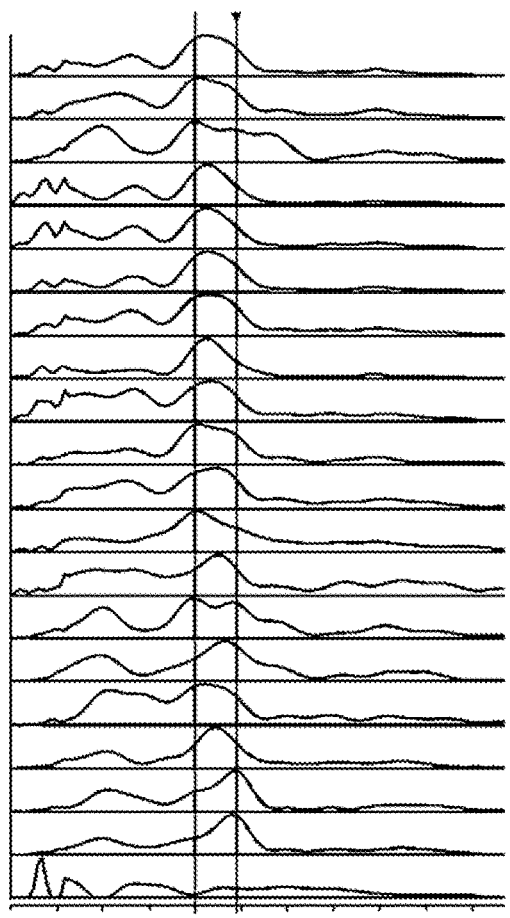
FIG. 5D is a graph diagram illustrating an example baseline analog EEG data set of a subject converted into a digital EEG data set according to an embodiment of the invention.
Figure 5E:
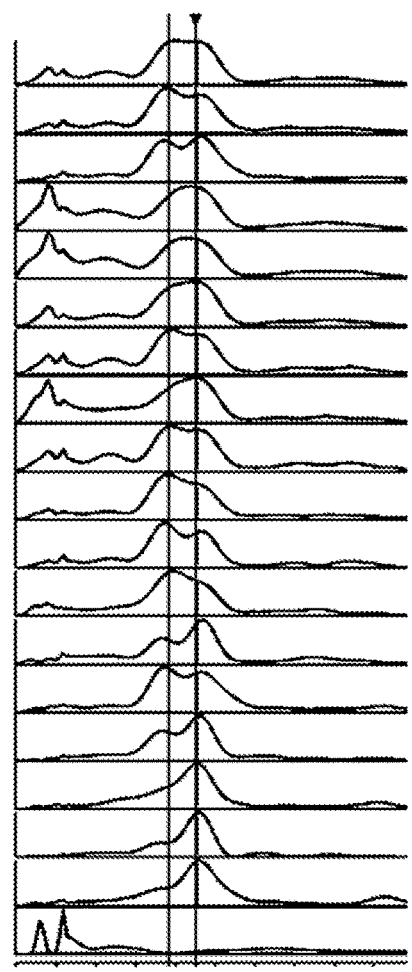
FIG. 5E is a graph diagram illustrating an example analog EEG data set from the subject of FIG. 5D converted into a digital EEG data set one month after the baseline EEG according to an embodiment of the invention.

FIG. 5D is a graph diagram illustrating an example baseline analog EEG data set of a subject converted into a digital EEG data set according to an embodiment of the invention. In the illustrated embodiment, the digital EEG data set corresponds to a baseline EEG for a subject prior to an initial personalized resonant frequency TMS treatment. FIG. 5E is a graph diagram illustrating an example analog EEG data set from the subject of FIG. 5D converted into a digital EEG data set acquired one month after the baseline EEG according to an embodiment of the invention. FIG. 5F is a graph diagram illustrating an example analog EEG data set from the subject of FIG. 5D converted into a digital EEG data set acquired two months after the baseline EEG according to an embodiment of the invention. As can be seen in FIG. 5F, coherence of the ODI peaks is nearly complete, resulting in a substantially vertical CDI for the subject. As compared to an ideal EEG data set shown in FIG. 5G, the subject's two month CDI is nearly ideal.

FIG. 5H is a block diagram illustrating an example set of neurobattery test scores 495 for a subject during a 9 week treatment plan according to an embodiment of the invention. In the illustrated embodiment, the subjective neurobattery test scores represent substantial progress for the subject from week 1 to week 9 across all five of the neurobattery tests.

Figure 6:
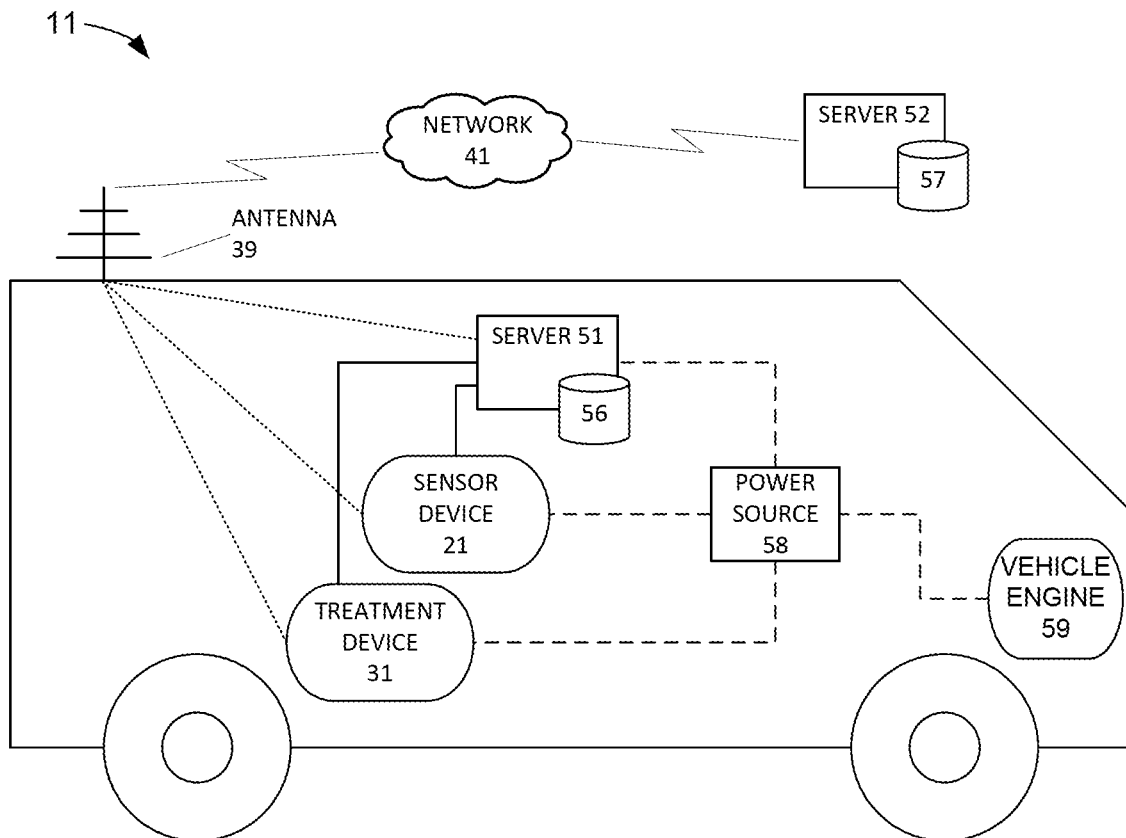
FIG. 6 is a block diagram illustrating an example mobile system for EEG based TMS treatment according to an embodiment of the invention.

FIG. 6 is a block diagram illustrating an example mobile system 11 for EEG based TMS treatment according to an embodiment of the invention. In the illustrated embodiment, the system 11 includes a sensor device 21 that is communicatively coupled with a server device 51 and/or a server device 52. Communication between the sensor device 21 and the server device 51 and/or 52 may be direct (e.g., through a direct wired or wireless connection) or via a wired or wireless data communication network 41. The network 41 may be a private network or a public network or any combination of public and private networks including for example, the Internet. The sensor device 21 can be any type of device capable of sensing EEG information from a subject and providing the sensed EEG information (e.g., analog signals). In one embodiment, the sensor device 21 comprises a plurality of leads that each sense EEG information from a separate region of the brain of the subject. For example, the sensor device 21 may include seven leads.

The system 11 also includes a treatment device 31 that is communicatively coupled with the server device 51 and/or 52. Communication between the treatment device 31 and the server device 51 and/or 52 may be direct (e.g., through a direct wired or wireless connection) or via the previously described data communication network 41. The treatment device 31 can be any type of device capable of delivering transcranial magnetic stimulation to the brain cells of a subject. In one embodiment, the treatment device 31 comprises a plurality of stimulators that each stimulate a separate region of the brain of the subject.

In one embodiment, the sensor device 21 and the treatment device 31 can be combined into a single sensor/treatment apparatus 36 that is capable of both sensing EEG information from the brain of the subject and stimulating the brain of the subject. In such an embodiment, the combined sensor/treatment apparatus 36 may be a single integrated unit or the combined sensor/treatment apparatus 36 may comprise a separate sensor device 21 and a separate treatment device 31 that are each worn simultaneously by the subject and that each operate simultaneously in connection with the server 51 and/or 52.

In the illustrated embodiment, the server 51 is resident within the mobile system 11 while the server 52 is remote from the mobile system 11 and communicatively coupled with one or more elements of the mobile system 11 via an antenna 39 and a network 41. Each of the servers 51 and/or 52 may comprise the same operational modules as previously described with respect to FIG. 1 and accordingly the description of such modules will not be repeated with respect to the present embodiment. Advantageously, in one embodiment, the server 51 may offload certain operations to the server 52 to reduce power consumption and/or complex processing in the mobile system 11. Additionally, as previously described the servers 51 and/or 52 are each configured with respective data storage areas 56 and/or 57 that include at least one non-transitory computer readable medium. In one embodiment, data from the server 51 may be communicated via the network 41 for storage in the data storage area 57 of the server 52.

In the illustrated mobile system 11 for EEG based TMS treatment, the sensor device 21, treatment device 31 and the server device 51 are each powered by a local power source 58. The local power source may be one or more batteries, a generator (e.g., a carbon based fuel power generator, a hydrogen generator, a solar power generator, etc.) a vehicle engine or the like. The power source may also include one or more power converters to provide appropriate power to the individual sensor device 21, treatment device 31 and server device 51. Advantageously, the sensor device 21, treatment device 31 and server device 51 may be configured to be powered directly by their own power sources, for example one or more dedicated batteries.

In operation, the mobile system 11 for EEG based TMS treatment may be any type of vehicle that is capable of propelling itself via land, water or air. For example, the mobile system 11 for EEG based TMS treatment may be a car, a truck, a helicopter, an airplane, a boat or a submarine, just to name a few.

Figure 7:
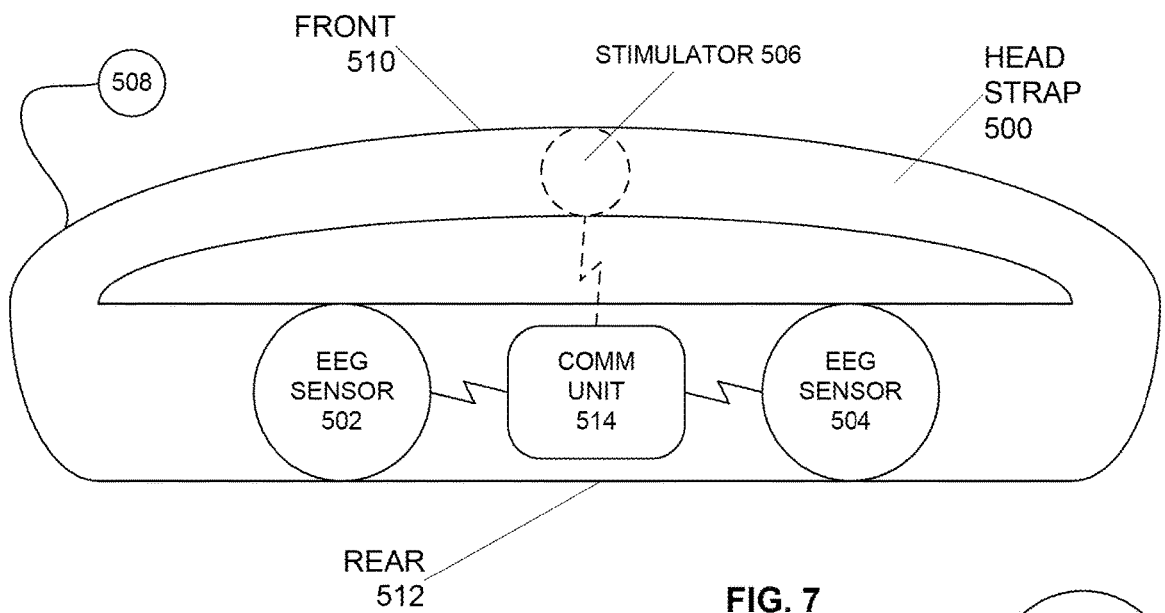
FIG. 7 is a block diagram illustrating an example sensor device according to an embodiment of the invention.

FIG. 7 is a block diagram illustrating an example sensor device 500 according to an embodiment of the invention. In the illustrated embodiment, the sensor device 500 is shown in the form of a headstrap 500. In alternative embodiments, the sensor device 500 can be any sort of wearable device capable of sensing EEG information from a subject. The headstrap 500 comprises a strap that is configured to be secured to the head of a subject and the strap supports and positions one or more EEG sensors 502 and 504. Although the illustrated embodiment shows two EEG sensors 502 and 504, it will be understood by the skilled artisan that one or more EEG sensors may be employed. In one embodiment, the EEG sensors 502, 504 are attached to the headstrap 500 in the rear 512 region of the headstrap 500 in order to position the EEG sensors 502, 504 for collection of alpha brain waves from the subject.

The headstrap 500 includes a ground node 508 that is configured to electrically ground the various components of the headstrap 500. In one embodiment, the ground node 508 is configured to attach to the earlobe of the subject. In one embodiment, the headstrap 500 has one or more transcranial magnetic stimulators 506 that are configured to deliver a stimulus to the subject. Although the illustrated embodiment shows only one stimulator 506, it will be understood by the skilled artisan that one or more stimulators may be employed. In one embodiment, the stimulator 506 is positioned to stimulate the subject at the FZ location, although other locations may also be selected. In an alternative embodiment, the stimulator may be configured to move along the headstrap 500 to different positions around the calvarium in order to stimulate different regions of the brain.

In the illustrated embodiment, the headstrap 500 also has a communication unit 514 that is electrically and/or communicatively coupled with the EEG sensors 502, 504 and the optional stimulator 506 and the ground 508. The communication unit 514 is configured to receive EEG data from the EEG sensors 502, 504 and send the EEG data to another device, for example server 50 or user device 515 that will be described with respect to FIG. 8. The communication unit 514 may optionally be configured to receive a treatment protocol from another device, e.g., the server 50, and provide an instruction based on the received treatment protocol to the stimulator 506 to cause the stimulator 506 to deliver one or more transcranial magnetic stimulations to the subject.

Figure 8:
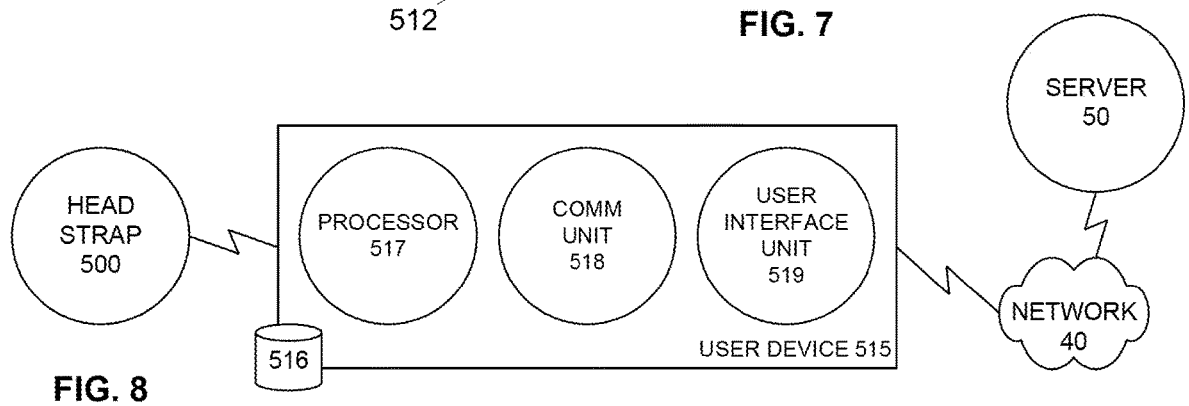
FIG. 8 is a block diagram illustrating an example sensor device in communication with an example user device according to an embodiment of the invention.

FIG. 8 is a block diagram illustrating an example sensor device 500 in communication with an example user device 515 according to an embodiment of the invention. In the illustrated embodiment, the sensor device 500 is shown in the form of a headstrap 500. In alternative embodiments, the sensor device 500 can be any sort of wearable device capable of sensing EEG information from a subject. In the illustrated embodiment, the headstrap 500 is communicatively coupled with user device 515 via a direct wired or wireless communication link. However, the user device 515 may alternatively be communicatively coupled with the headstrap 500 by any suitable means for data communication. The user device 515 may also be communicatively coupled with the network 40 and thereby in communication with any of the previously described elements of the system 10 or the mobile system 11 via the network 40, such as the server 50. In the illustrated embodiment, the user device 515 comprises a data storage area 516, a processor 517 a communication unit 518 and a user interface unit 519. In various embodiments, the user device 515 be any sort of processor enabled device capable of communication with the sensor device 500, for example a laptop computer, a tablet computer, a cell phone, a watch, and the like.

In one embodiment, the headstrap 500 senses EEG data from the brain of the subject and provides the data to the user device 515 via the communication unit 514 on the headstrap 500 and the communication unit 518 on the user device. The user device 515 may be used by a physician or other medical professional or by the subject. In one embodiment, the communication unit 518 is implemented as an external dongle (not shown) that is connected to the user device 515 and the communication unit 518 is configured to cooperatively manage communications between the headstrap 500 and the user device 515 by coordinating with the communication unit 514 of the headstrap 500.

The processor 517 on the user device 515 is configured to receive the sensor data received from the headstrap 500 and process the sensor data to generate real time user interface information that can be provided for presentation on a display or delivery by some other user interface such as audio or haptic. In one embodiment, the real time user interface information is continuously provided to the user interface unit 519 for initial delivery (e.g., presentation on a display or audio or haptic delivery) and real time updating of the delivery of the information (e.g. presentation on the display or audio or haptic delivery). In one embodiment, the user interface device 515 is configured as mobile computer device such as a laptop device or a tablet device or a touchscreen device or a mobile phone device or a watch device. Advantageously, such an embodiment allows a user to monitor her "in the zone" status during any activity where optimal human performance is desired. For example, studying, test taking, athletics, operating vehicles and/or machinery, etc.

In one embodiment, a kit is provided that includes a sensor device 500 (e.g., a headstrap or other wearable device) in combination with a software application configured to run on a mobile communication device 515 of the user (e.g., mobile phone, smart watch, etc.). The software application is configured to execute on a processor of the mobile communication device 515 and receive EEG data from the sensor device 500. The software application is also configured to process the EEG data to determine a current personalized resonant frequency for the subject and provide the current personalized resonant frequency information to the subject via a user interface of the mobile communication device 515.

Figure 9:
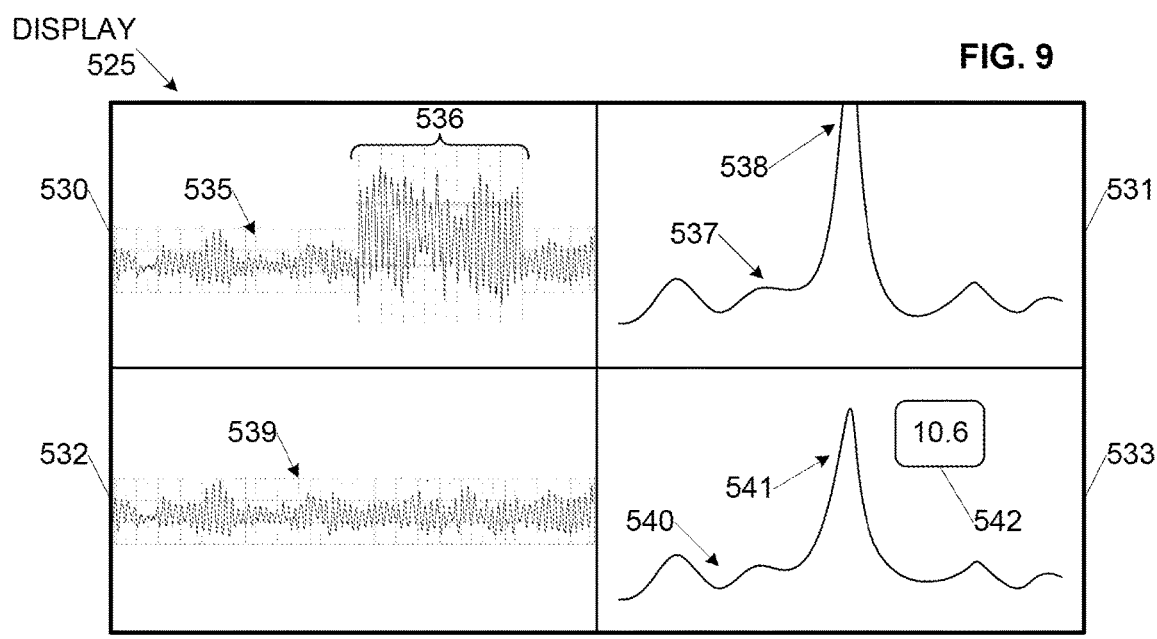
FIG. 9 is a block diagram illustrating an example user interface presented on a display according to an embodiment of the invention.

Turning to FIG. 9, in one embodiment, the real time user interface that is presented on a display 525 of the user device 515 is divided into four quadrants, namely 530, 531, 532 and 533. Each quadrant 530, 531, 532 and 533 presents different, but related information. In quadrant 530, the raw EEG signal 535 is presented in real time and the raw EEG signal 535 scrolls across the portion of the display 525 that is devoted to quadrant 530. If the subject is presently being treated with TMS, some portion of the raw EEG signal 535 may form a very visible spike range 536 that is caused by signal noise picked up by the EEG sensors (e.g., sensors 502 and 504) from the one or more TMS stimulators (e.g., stimulator 506).

In quadrant 531, a raw EEG graph 537 of the raw EEG signal is presented in real time. The raw EEG signal 535 is processed (e.g., by Fourier transform) to generate the raw EEG graph 537 that scrolls across the portion of the display 525 that is devoted to quadrant 531. The raw EEG graph 537 generally forms a raw peak 538 that can grossly spike well beyond the portion of the display 525 that is devoted to quadrant 531 in the presence of signal noise from TMS stimulation as previously described.

In quadrant 532, a processed EEG signal 539 is presented in real time and the processed EEG signal 539 scrolls across the portion of the display 525 that is devoted to quadrant 532. The raw EEG signal 535 is processed to generate the processed EEG signal 539. Advantageously, processing of the raw EEG signal 535 removes any signal noise, for example caused by caused by the one or more TMS stimulators (e.g., stimulator 506). Accordingly, as the processed EEG signal 539 scrolls across the portion of the display 525 that is devoted to quadrant 532, there are no visible spike ranges caused by TMS stimulators.

In quadrant 533, a processed EEG graph 540 is presented in real time and the processed EEG graph 540 scrolls across the portion of the display 525 that is devoted to quadrant 533. The processed EEG signal 539 is further processed (e.g., by Fourier transform) to generate the processed EEG graph 540. The processed EEG graph 540 generally forms a processed peak 541, however, even when the subject is presently being treated with TMS, the processed peak 541 does not grossly spike because any signal noise picked up by the EEG sensors (e.g., sensors 502 and 504) from the one or more TMS stimulators (e.g., stimulator 506) has already been removed from the processed EEG signal 539. Advantageously, this allows for a real time presentation of the processed EEG graph 540 and its corresponding peak 541 on the display 525 while the subject is wearing the headstrap 500. In one embodiment, a personalized resonant frequency brain wave value 542 is also presented on the display 525 in quadrant 533 near the peak 541 of the processed EEG graph 540. One advantage of presenting the personalized resonant frequency brain wave value 542 is to validate the calculated personalized resonant frequency brain wave value 542 against the frequency being delivered under the treatment protocol.

One significant advantage of the real time processing of EEG data before during and after TMS stimulation is to determine a subject's minimum neuronal activation threshold. For example, during TMS stimulation, the amplitude at which treatment is provided may be slowly reduced while monitoring the number of neurons that are activating at the desired frequency (i.e., the frequency of the TMS stimulation). In one embodiment, the number of neurons that are activating at the desired frequency correlates to the height and width of the processed EEG graph 540. As the amplitude of the TMS stimulation is reduced, the number of neurons that are being recruited by the TMS stimulation to activate at the desired frequency (as detected by the EEG sensors) is similarly reduced. When the number of neurons that are being recruited by the TMS stimulation to activate at the desired frequency reduces to the point where the amplitude of the TMS stimulation is insufficient to cause the neurons to activate, the minimum neuronal activation threshold is identified. Significant advantages of delivering TMS treatment at or slightly above the minimum neuronal activation threshold include decreased overstimulation of neurons, decreased pain to the subject, decreased refractory period of neurons (e.g., a neuron can activate again more quickly), decreased risk of seizure, ability to treat more sensitive areas of the brain (e.g., motor strip) and a stronger and more durable therapeutic response from the subject.

Turning back to FIG. 8, in one embodiment, the user device 515 may be configured as a mobile communication device such as a cell phone, a tables or a watch. In such an embodiment, the user device 515 may be configured to provide a readout of the current personalized resonant brain frequency value 542 of the subject, with or without the processed EEG graph 540. Furthermore, in one embodiment the user interface unit 519 of the user device 515 is configured to receive an input from the subject and store in memory 516 an indication that the subject was "feeling good" or feeling "in the zone" at that particular moment time. Information included in the stored indication may include raw EEG data, processed EEG data, a timestamped personalized resonant brain frequency value and any desired environmental information corresponding to the indication such as the heart rate of the subject, which may be collected, e.g. by a watch format of the user device 515. Plural indications can be stored over time and these plural indications and their respective personalized resonant brain frequency values can be analyzed to derive or determine the subject's optimal personalized resonant brain frequency value.

Additionally, the processor 517 on the user device 515 may analyze historical indications to determine an optimized personalized resonant brain frequency value that is personalized for the subject. The indications stored in memory 516 may also be provided to the server 50 or another device (not shown) for such analysis or for other analysis. In addition to determining an optimized personalized resonant brain frequency value that is personalized for the subject, an optimized personalized resonant brain frequency value range may also be determined for the subject. Additionally, such analysis may also determine optimized personalized resonant brain frequency values for different times of day and different days of the week for a subject based on historical analysis.

Example Embodiments

In one embodiment, headstrap 500 is used to implement an objective concussion protocol. For example, the headstrap 500 senses EEG data from a subject who suffered a head related injury and provides the EEG data to a companion device such as the user device 515 or the server 50 for analysis. The analyzed EEG data includes a current personalized resonant brain frequency value for the injured subject that can be compared to a predetermined personalized resonant brain frequency value for the subject that was predetermined when the subject was not injured. Comparison of the current and predetermined personalized resonant brain frequency values advantageously provides an objective measurement to assess the ability of the subject to return to regular activity (e.g., work, sports, etc.).

In one embodiment, the headstrap 500 is used to sense EEG data from a subject to evaluate the subject for suitability to perform a function (e.g., a job function). For example, in one embodiment, a vehicle driver subject wears the headstrap 500 and the EEG data is provided to the user device 515 (e.g., located in the vehicle). The user device 515 may analyze the EEG data or provide the EEG data to another device (e.g., server 50 located remote from the user device 515) for analysis. The EEG data can be processed to determine a current personalized resonant brain frequency value for the subject and compare it to a predetermined personalized resonant brain frequency value (or predetermined personalized resonant brain frequency value range) to determine the suitability of the subject to perform a job function such as driving the vehicle. Additional job functions may include taking off or flying or landing an airplane, operating heavy equipment, performing surgery, etc. In this fashion, a subject can be remotely monitored and notified whether or not to perform a task and the subject may also be notified when it is time to rest, or eat, or take some other action to improve the current personalized resonant brain frequency value of the subject.

Alternatively, the comparison of the current personalized resonant brain frequency value to the predetermined personalized resonant brain frequency value or range allows for the subject to selectively perform tasks when the subject is "in the zone" or otherwise operating in a desired state for the task. Accordingly, the system allows for optimization of performance of certain tasks and/or improved efficiency of performance of certain tasks.

In one embodiment, a user subjectively declares by way of input to the user device 515 that the user is feeling "in the zone" and the device 515 records the current personalized resonant brain frequency value in response to the input. Advantageously, the device 515 may average the various "in the zone" values recorded over time to determine an "in the zone" range for the specific user. This range may be continuously updated and correlated to environmental characteristics (time of day, lightness/darkness, etc.) to provide the user with personalized "in the zone" information to allow the user to optimize task selection.

In one embodiment, the treatment location (mobile or otherwise) includes a computer device (e.g., server 50 or user device 515) that is configured to access an electronic medical record ("EMR") for the subject (via a network or a local stored copy of the EMR) and use the historical EEG data, personalized resonant brain frequency value data, subject indication data, and treatment information as part of an analysis of the subject to determine a current treatment protocol. Advantageously, the system 10 or 11 is also configured to store newly acquired EEG data and any treatments applied to the subject back to the EMR, for example via network 40.

In one embodiment, the system 10 or 11 is advantageously able to treat the motor function areas of the brain because the stimulation provided by the treatment device 30 (e.g., one or more stimulators 506) is delivered at a significantly lower threshold than conventional TMS treatments and repetitive TMS (rTMS) treatments. Treatment of the motor function areas of the brain is not done using conventional rTMS or TMS treatment technology because doing so would potentially harm the subject.

A method of delivering personalized repetitive TMS (PRTMS) treatment includes giving the subject 30-40 grams of sugar before PRTMS treatment. The purpose of giving the subject sugar is to increase the glucose in the bloodstream. Glucose in the bloodstream is used by the brain during activity and therefore improves the PRTMS treatment. In one embodiment.

In one embodiment, the server 50 is configured to analyze the EEG data of a subject and diagnose a condition of the subject based on the EEG data alone or alternatively based on the EEG data in combination with neuro-battery information. Conditions that can be diagnosed by the server 50 include heart arrhythmias and irritable bowel syndrome (IBS). For IBS, the server 50 is configured to receive and analyze electrogastrogram (EGG) data in combination with the EEG data and/or the neuro-battery information. Advantageously, heart arrhythmias may be reduced or ablated by harmonizing the personal resonant frequency of a subject through PRTMS treatment.

In one embodiment, the user device 515 is configured to receive EGG data from an EGG apparatus (not shown) connected to the subject while simultaneously receiving EEG data from the headstrap 500. In this embodiment, the user device 515 is also configured to analyze the EEG data and present a personalized resonant frequency value that is updated in real time during treatment of the subject by the treatment device 30 in order to visualize real time changes to the personalized resonant frequency value that is responsive to treatments applied to the brain of the subject by the treatment device 30.

Example Treatments

The disclosed systems and methods can be used to treat a wide variety of conditions, including but not limited to those set forth in Table 1 and Table 2 below.

TABLE 1

| Organic Injury | Nociceptive | Orthographic |
| --- | --- | --- |
| Cerebral Palsy | Migraine | Chemobrain |
| Stroke | Tinnitus | Opioid Dependence |
| Traumatic Brain Injury | Chronic Back Pain | PTSD |
| Concussive Syndrome | Chronic Neck Pain | |
| Brain tumors patients | Fibromyalgia | |

TABLE 2

| Neurodevelopmental | Neurodegenerative | Psychological |
| --- | --- | --- |
| Autism | Alzheimer's | Anxiety |
| Epilepsy | Parkinson's | Depression |
| Schizophrenia | Lyme's Disease | Bipolar Disorder |
| Tourette's | Dementia | Obsessive-Compulsive Disorder |
| ADHD | | Addiction Disorders |

Figure 10:
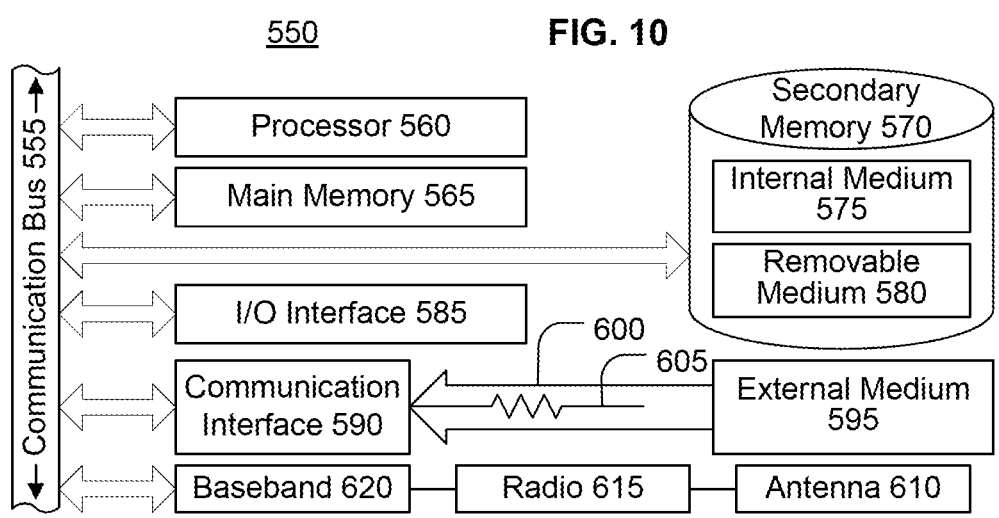
FIG. 10 is a block diagram illustrating an example wired or wireless processor enabled device that may be used in connection with various embodiments described herein.

FIG. 10 is a block diagram illustrating an example wired or wireless system 550 that may be used in connection with various embodiments described herein. For example the system 550 may be used as or in conjunction with a sensor device, treatment device, combined sensor/treatment device, server device, power source device, user interface device or user device or any other device as previously described with respect to the drawings. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An electroencephalogram (EEG) evaluation system comprising:
 a headstrap configured to be secured to a head of a subject;
 one or more sensor devices attached to headstrap and positioned to sense a brain wave of the subject and generate analog electroencephalogram (EEG) signals corresponding to the subject;
 a user device communicatively coupled with the one or more sensor devices, the user device configured to:
 receive the analog EEG signals corresponding to the subject from the one or more sensor devices, process the analog EEG signals, and generate a processed real time EEG signal;
 determine a real time brain frequency value based on an analysis of at least the processed real time EEG signal;
 present on a display a real time brain frequency value graph based on the processed real time EEG signal; and
 identify a minimum neuronal activation threshold for the subject, wherein the minimum neuronal activation threshold is determined based on first peak frequencies for one or more leads of the one or more sensor devices by systematically lowering a treatment amplitude of a Transcranial Magnetic Stimulation (TMS) treatment protocol until the first peak frequencies reflect insufficient neuronal recruitment at a target frequency;
 wherein the user device is configured to determine the TMS treatment protocol for the subject comprising at least a frequency based on a personalized resonant brain frequency and the treatment amplitude based on the minimum neuronal activation threshold for the subject; and
 wherein the stimulus is based on the TMS treatment protocol.

2. The system of claim 1, wherein the user device is one of a mobile computer, a tablet, a wireless communication device, a watch, or a laptop.

3. The system of claim 1, further comprising a transcranial magnetic stimulator attached to the headstrap and positioned to deliver a stimulus to a brain of the subject, wherein the stimulus is based at least in part on the minimum neuronal activation threshold.

4. The system of claim 3, wherein the user device is further configured to determine a personalized resonant brain frequency of the of the subject based at least in part on the analog EEG signals, the processed real time EEG signal, the real time brain frequency value graph, or a combination thereof; and wherein the stimulus is based at least in part on the personalized resonant brain frequency.

5. The system of claim 1, wherein the user device is further configured to determine the personalized resonant brain frequency based at least in part on the analog EEG signals, the processed real time EEG signal, the real time brain frequency value graph, or a combination thereof.

6. The system of claim 3, wherein the transcranial magnetic stimulator is positioned to deliver the stimulus to an FZ location of the brain of the subject.

7. The system of claim 1, further comprising a ground node configured to attach to the subject.

8. The system of claim 1, wherein the user device is further configured to present on the display the personalized resonant brain frequency value.

9. The system of claim 1, wherein the user device is further configured to continuously update the real time brain frequency value presented on the display in accordance with the received analog EEG signals.

10. An apparatus comprising:
    a headstrap configured to be secured to a head of a subject;
    one or more sensor devices attached to the headstrap and positioned to sense a brain wave of the subject and generate electroencephalogram (EEG) signals corresponding to the subject; and
    a transcranial magnetic stimulator attached to the headstrap and positioned to deliver a stimulus to a brain of the subject,
    wherein the apparatus is communicatively coupled to a user device;
    wherein the user device is configured to identify a minimum neuronal activation threshold for the subject, wherein the minimum neuronal activation threshold is determined based on first peak frequencies for one or more leads of the one or more sensor devices by systematically lowering a treatment amplitude of a Transcranial Magnetic Stimulation (TMS) treatment protocol until the first peak frequencies reflect insufficient neuronal recruitment at a target frequency; and
    wherein the user device is configured to determine the TMS treatment protocol for the subject comprising at least a frequency based on a personalized resonant brain frequency and the treatment amplitude based on the minimum neuronal activation threshold for the subject; and
    wherein the stimulus is based on the TMS treatment protocol.

11. The apparatus of claim 10, wherein the apparatus is configured to:
    receive analog EEG signals corresponding to the subject from the one or more sensor devices, process the analog EEG signals, and generate a processed real time EEG signal;
    determine a real time brain frequency value based on an analysis of at least the processed real time EEG signal; and
    present on a display a real time brain frequency value graph based on the processed real time EEG signal.

12. The apparatus of claim 11, wherein the user device is further configured to determine the personalized resonant brain frequency based at least in part on the analog EEG signals, the processed real time EEG signal, the real time brain frequency value graph, or a combination thereof.

13. The apparatus of claim 10, wherein the transcranial magnetic stimulator is positioned to deliver the stimulus to an FZ location of the brain of the subject.

14. The apparatus of claim 10, further comprising a ground node configured to attach to the subject.

* * * * *